US005599690A

United States Patent [19]
Fenton et al.

[11] Patent Number: 5,599,690
[45] Date of Patent: Feb. 4, 1997

[54] CONTROL OF NORLEUCINE INCORPORATION INTO RECOMBINANT PROTEINS

[75] Inventors: Dennis Fenton, Newbury Park; Por-Hsiung Lai, Westlake Village; Hsieng Lu, Thousand Oaks; Michael Mann, Thousand Oaks; Larry Tsai, Thousand Oaks, all of Calif.

[73] Assignee: Amgen Inc., Thousand Oaks, Calif.

[21] Appl. No.: 363,862

[22] Filed: Dec. 22, 1994

Related U.S. Application Data

[63] Continuation of Ser. No. 880,462, May 5, 1992, abandoned, which is a continuation of Ser. No. 151,170, Feb. 1, 1988, abandoned.

[51] Int. Cl.$^6$ .............................. C12P 21/02; C12P 21/04
[52] U.S. Cl. .................... 435/69.1; 435/69.5; 435/69.51; 435/69.52
[58] Field of Search .......................... 435/172.3, 252.33, 435/69.1, 71.2, 69.5, 69.51, 69.52; 935/12; 530/304

[56] References Cited

U.S. PATENT DOCUMENTS

| 3,978,035 | 8/1976 | Wunsch et al. | 260/112.5 |
| 4,356,270 | 10/1982 | Itakura | 435/317 |
| 4,568,640 | 2/1986 | Rubin | 435/70 |

FOREIGN PATENT DOCUMENTS

| 136490 | 4/1985 | European Pat. Off. |
| 136489 | 4/1985 | European Pat. Off. |
| 0199568 | 10/1986 | European Pat. Off. |
| WO83/04053 | 11/1983 | WIPO |
| WO87/01132 | 2/1987 | WIPO |

OTHER PUBLICATIONS

Hassaw et al. 1952, Arch. Bioichem. Biophs. 129–137.
Black et al. 1955, J. Am. Chem. Soc. 77, 6082–6083.
Caluo, J. M. 1983, In: Amino Acids Biosynthesis And Genetic Regulation, pp. 267–268, Addison–Wesley Publishing Co. Reading, Mass.
Kempe, et al Gene 39: 239–245, 1985.
Trupin, et al. B.B.R.C. 24(1):50–55, 1966.
Kisumi, et al. J. Biochem. (Tokyo) 80:333–339, 1976.
Kaufman et al., "Coamplification and Coexpression of Human Tissue–Type Plasminogen Activator and Murine Dihydrofolate Reductase Sequences in Chinese Hamster Ovary Cells", Molecular and Cellular Biology, vol. 5, No. 7, pp. 1750–1759 Jul. 1985.
Cate et al., "Isolation of the Bovine and Human Genes for Mullerian Inhibiting Substance and Expression of the Human Gene in Animal Cells", Cell, vol. 45, pp. 685–698 Jun. 06, 1986.
Adelberg, J. Bacteriol. 76, 326 (1958).
Barber et al., Chem. Commu. 325–329 (1981).
Black et al., J. Am. Chem. Soc. 77, 6082–6083 (1955).
Calvo, J. M., "Leucine Biosynthesis in Procaryotes" in Amino Acids: Biosynthesis and Genetic Regulations, J. M. Herrmann and R. L. Somerville, etds. Addison–Wesley Publishing, 267–268 (1983).
Hassan et al., Arch. Biochem. Biophys. 39, 129–137 (1952).
Hewick et al., J. Biol. Chem. 256, 7990–7997 (1981).
Hobson, J. Gen. Microbiol. 82, 425–429 (1974).
Hunkapiller, et al., Science 219, 650–659 (1983).
Kisumi et al., Appl. Envir. Microbiol. 34, 135–138 (1977).
Kisumi et al., J. Biochem. 80, 333–339 (1976).
Lai, Anal. Chim. Acta. 163, 243–248 (1984).
Lawrence, J. Bacteriol. 109, 8–11 (1972).
Lemoine et al., Eur. J. Biochem. 4, 213–221 (1968).
Miller, J. H., Experiments in Molecular Genetics, Cold Spring Harbor Laboratory, 121–139 (1972).
Sherman et al., Bioessays 3, 27–31 (1985).
Tsai, et al., J. Indust. Micro. 2, 181–187 (1987).

*Primary Examiner*—George C. Elliott
*Attorney, Agent, or Firm*—Robert B. Winter

[57] ABSTRACT

Norleucine incorporation into recombinant gene products may be inhibited by culturing the cells expressing the gene products in media comprising a high level of leucine and/or methionine, or by expressing the gene products in a leu mutant. Norleucine incorporation in recombinant gene products may be promoted by culturing the cells expressing the gene products in media comprising norleucine or deficient in leucine and/or methionine. For example, norleucine analogs of IL-2, GCSF, γ-interferon and α-consensus interferon may be produced in this way.

19 Claims, 1 Drawing Sheet

CONTROL OF NORLEUCINE INCORPORATION INTO RECOMBINANT PROTEINS

This application is a continuation, of application Ser. No. 07/880,462, filed May 5, 1992, abandoned, which is a continuation of application Ser. No. 07/151,170 filed on Feb. 1, 1988, now abandoned.

BACKGROUND OF THE INVENTION

The present invention pertains in general to methods for controlling incorporation of amino acids in expressed recombinant proteins and analogs produced thereby. In particular, the present application pertains to methods for control of norleucine incorporation into recombinant proteins and to analogs of the recombinant proteins produced thereby.

Norleucine may be utilized as a substrate for *E. coli* methionyl tRNA synthetase, although its $K_m$ is 200-fold higher than that for methionine [Lemoine et al., *Eur. J. Biochem.*, 4, 213–221 (1968)]. Norleucine is a methionine antagonist in many microorganisms [Adelberg, *J. Bacteriol.*, 76, 326 (1958), Hobson, *J. Gen. Microbiol.*, 82, 425–429 (1974), and Lawrence, *J. Bacteriol.*, 109, 8–11 (1972)] and may be synthesized in *Serratia marcessens* [Kisumi et al., *J. Biochem.*, 80, 333–339 (1976)]. Exogenous radioactively-labelled norleucine may be incorporated into casein proteins when fed to cows [Black et al., *J. Am. Chem. Soc.*, 77, 6082–6083 (1955)]. However, the endogenous occurrence of norleucine in microbial proteins, in particular in recombinant DNA-derived proteins has never been reported.

Kisumi et al. found accumulation of norleucine in a norleucine-resistant mutant of *Serratia marcessens* [Kisumi et al., *Appl. Envir. Microbiol.*, 34, 135–138 (1977)]. Kisumi et al., *J. Biochem.*, 80, 333–339 (1976) postulated that in *Serratia marcesens*, norleucine was synthesized via a leucine biosynthetic pathway in which α-ketobutyrate, α-ketovalerate, and α-ketocaproate are substrates in the sequential steps of enzymatic synthesis including a step catalyzed by α-isopropylmalate synthetase and other enzymes such as isopropyl malate dehydratose, or isopropyl malate dehydrogenase. The final step of leucine synthesis in *Serratia marcessens* is catalyzed by leucine transaminase. To synthesize these linear α-ketoacids, acetyl CoA is used in the chain elongation process in the microorganism [Metzler, *Biochemistry*, "The Chemical Reactions of Living Cells", Academic Press, New York, 1977], but at the present time, it is not known what caused the unusual linear chain elongation reported for these α-ketoacids.

Wunsch et al., U.S. Pat. No. 3,978,035 describes a method of synthetically producing L-norleucine-13-motilin. The method of Wunsch et al. is based on the replacement of the L-methionine residue located in the 13-position by an L-norleucine residue. This complex chemical synthesis uses the N, N'-dicyclohexylcarbodiimide-N-hydroxysuccinimide method to connect fragments I to VI. A masked polypeptide containing the amino acid sequence is split off from the protective groups with trifluoroacetic acid and then the trifluoracetate and bromide ions are removed.

Rubin, U.S. Pat. No. 4,568,640 describes a method of substituting one amino acid for another in a protein chain to improve selected properties of the protein. The tRNA is modified to carry the substituting amino acid. Modification of the selected tRNA is by misacylation which is facilitated by dimethylsulfoxide, cacodylate and methanol.

SUMMARY OF THE INVENTION

The present invention relates to controlling the incorporation of norleucine in recombinant-derived proteins. More specifically, the presence or absence of norleucine can be regulated by varying the concentration of methionine and/or leucine and/or norleucine. By such means, norleucine-containing analogs of recombinant-derived protein can be obtained. Further, the absence of norleucine can be achieved by expressing the gene for the desired recombinant-derived protein in cells unable to synthesize leucine.

The present invention provides a recombinantly-derived polypeptide containing norleucine. In general, the present invention provides polypeptides which include endogenous incorporation of norleucine. More specifically, the present invention provides norleucine-containing analogs of interleukin-2, granulocyte colony stimulating factor, γ-interferon and α-consensus interferon.

A method according to the present invention inhibits incorporation of norleucine, in place of methionine, in an expression product of a gene encoding a polypeptide containing methionine within a cell. This inhibition is accomplished by establishing a concentration of lecuine and/or methionine in a cell culture medium, which concentration is the minimum concentration required to prevent norleucine synthesis by a cell, and introducing the cell into a cell culture medium comprising greater than the established minimum concentration of leucine and/or methionine.

A method according to the present invention promotes incorporation of norleucine, in place of methionine, in an expression product of a gene encoding methionine within a cell. This promotion is accomplished by establishing a concentration of lecuine and/or methionine in a cell culture medium, which concentration is the minimum concentration required to prevent norleucine synthesis by a cell, and introducing the cell into a cell culture medium comprising less than the established minimum concentration of leucine and/or methionine. This promotion may also be accomplished by establishing a concentration of norleucine in a cell culture medium, which concentration is the minimum concentration required to allow incorporation of norleucine in place of methionine in a protein expressed by a gene encoding methionine within a cell, and introducing the cell into a cell culture medium having a greater concentration of norleucine than the established minimum concentration.

Another method according to the present invention inhibits incorporation of norleucine in place of methionine in an expression product of a gene encoding methionine within a cell. This inhibition is accomplished by expressing the gene in a cell unable to biosynthesize leucine.

DETAILED DESCRIPTION

Figure 1:
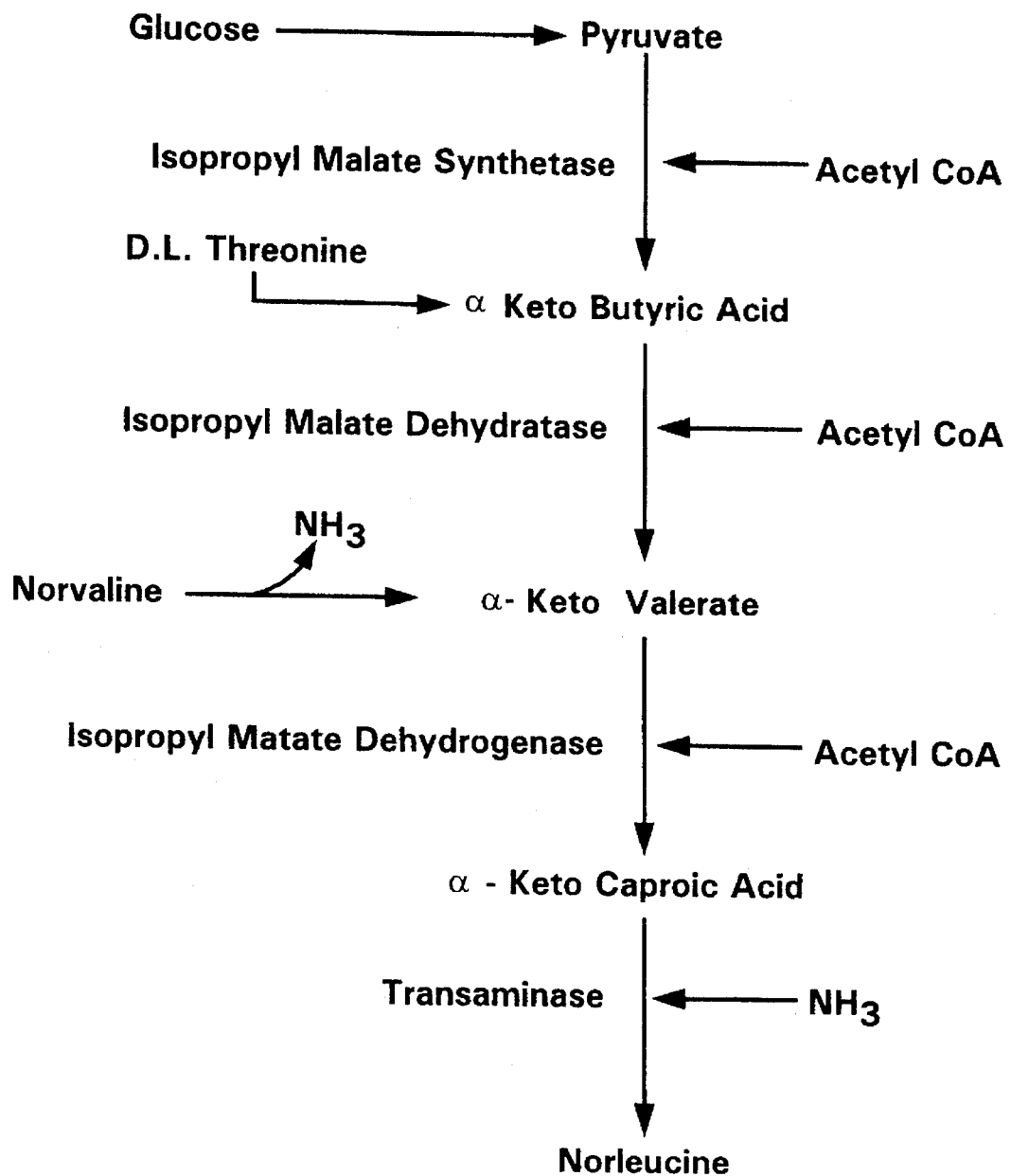
FIG. 1 is a flow chart depicting the proposed biosynthetic pathway for norleucine in *E. coli*. The arrows designated (a), (b) and (c) highlight the steps leading to norleucine incorporation.

Sequence determination of highly purified recombinant DNA-derived interleukin-2 (IL-2) produced by genetically modified *E. coli* revealed molecular heterogeneity at several amino acid positions where methionine is the amino acid residue encoded in the recombinant gene expressing the protein molecule. When compared to the amino acid sequence of native interleukin, an uncommon amino acid, norleucine (α-aminohexanoic acid), was found at three positions in place of methionine, including the NH$_2$-terminal position.

Identification of norleucine was based on Edman degradation of intact protein, isolation of norleucine-containing peptides, and characterization of the peptides using peptide sequencing and mass spectrometric analysis.

During high density fermentation in minimal medium of recombinant *E. coli* producing interleukin-2, immune interferon (γ-interferon), alpha consensus interferon (α-consensus interferon), or granulocyte colony stimulating factor (hG-CSF), the uncommon amino acid, norleucine was observed to be incorporated in the expressed recombinant protein product in variable amounts up to 22%. Norleucine is apparently synthesized de novo. It accumulates and competes with methionine for incorporation into protein via the aminoacylation of methionine transfer RNA.

Norleucine may be synthesized by an unusual reaction involving the enzymes of the leucine biosynthetic pathway. Adelberg, *J. Bacteriol.*, 76, 326 (1958). The biosynthetic pathway of norleucine has been proposed for the bacterium, such as *Serratia marcessens*. The enzymes normally transfer an acetyl function from acetyl CoA to α-ketoisovalerate to form α-ketoisocaproate for synthesizing L-leucine. However, the enzymes are not highly substrate specific, and other α-keto acids may serve as acetyl acceptors, such as pyruate, α-ketobutyrate, and α-ketovalerate. In the case of norleucine biosynthesis, α-ketobutyrate is converted to α-ketovalerate, which is in turn converted to α-ketocaproate. The α-ketocaproate is converted to norleucine by transamination as shown in FIG. 1.

A genetic approach to prevent norleucine incorporation eliminates the biosynthesis of norleucine in recombinant *E. coli* by inactivating one or more of the genes of the leucine biosynthetic pathway. The genes of this pathway include leuA, leuB, leuC and leuD. The genes may all be inactivated or they may be inactivated, singly or in combination. The growth of strains having such genetic modifications is permitted by addition of exogenous leucine during fermentation. This is readily accomplished by including a source of hydrolyzed protein in the growth medium. Gene inactivation may be effected by either chemical mutagenesis, radiation, or transposon mutagenesis techniques. See J. H. Miller, Experiments in Molecular Genetics, Cold Spring Harbor Laboratory, 1972, pp. 121–139. In addition, *E. coli* leucine mutants such as GCSC5539, a leuA mutant of *E. coli* K12, GCSC4695, a leuB mutant of *E. coli* K12, GCSC 5542, a leuC mutant of *E. coli* K12, and GCSC5544, a leuD mutant of *E. coli* K12, may be obtained from the *E. coli* Genetic Stock Center, New Haven, Conn.

This genetic approach is effective in eliminating norleucine in recombinant proteins produced in *E. coli*. This approach is believed to be applicable for other recombinant products and other host systems.

Norleucine incorporation into recombinant proteins may be also successfully inhibited or hindered by either adding leucine and/or methionine to a medium. A high level of leucine in the medium is believed to inhibit enzymes of the leucine synthetic pathway which are also involved in norleucine synthesis, while a high level of methionine is believed to favor its incorporation into protein over that of norleucine by providing an excess of methionine as a substrate for methionyl tRNA synthetase. Either approach blocks norleucine de novo synthesis in a host cell and reduces norleucine incorporation to an undetectable level. Levels of both methionine and leucine can also be added to the medium to inhibit or hinder norleucine incorporation.

Norleucine incorporation has been detected in the protein expression product of recombinant DNA rather than in native *E. coli* proteins. Incorporation of norleucine may be related to high intensity recombinant protein synthesis of the sort present during thermoinduction.

The present invention is revealed in more detail in the following Examples. In Example 1, recombinant interleukin-2 ("IL-2") is observed to include norleucine. In Example 2 the relationship of norleucine incorporation to fermentation conditions is explored. Example 3 discloses that norleucine is not found in native *E. coli* protein under conditions where norleucine is incorporated in recombinant gene products expressed in *E. coli*. In Example 4, the relationship between the level of norleucine incorporation and the rate of recombinant protein synthesis is explored. Example 5 compares norleucine incorporation in norvaline-fed *E. coli* with that found in norleucine-fed *E. coli*. Example 6 is an examination of the degree of incorporation of norleucine under fermentation in media containing norleucine and/or methionine. Example 7 is a description of genetic control of norleucine incorporation into a recombinant product by expression in a leuA mutant.

Published procedures for the construction of recombinant DNA-derived polypeptides provide the details of the expression of polypeptides. For example, a detailed description of expression vector systems is described in published European patent application No. 136,490. European patent application No. 136,489 describes the microbial expression of interleukin II and analogs. European patent applications No. 108,128 and No. 199,568 describe recombinant human interferon. A description of expression of granulocyte colony stimulating factor (GCSF) in a procaryotic or eucaryotic host cell is provided for in WO8701132 filed Feb. 26, 1987.

The high cell density fermentation to produce recombinant polypeptides in *E. coli* was carried out in a fedbatch mode in a 16 liter fermentor. Two fermentation processes for cell growth and product synthesis are utilized, single and dual feed systems. In the single feed system, the single feed medium (shown in Example 2) is added before and after induction. Supply of the single feed medium was initiated when the bacterial culture reached an optical density (OD) of 3.0 and was adjusted periodically based on OD. At an OD of approximately 30, the fermentor temperature was increased to 42° C. to induce synthesis of recombinant product. The single feed medium was maintained for the remainder of the fermentation at a fixed rate of 200 ml/hr. The fermentation was ended six (6) hours after the increase of temperature. In the dual feed system, the culture was fed during the course of fermentation with two different feed media. The growth of the bacterial culture was monitored for increase of optical density at appropriate intervals. Feed of medium #1 (shown in Example 2) was initiated when the bacterial culture reached an OD of 3.0. The feed of medium #1 was adjusted periodically based on the optical density of the culture. When the bacterial culture reached an OD of approximately 30, the fermentor temperature was increased to 42° C. to induce synthesis. Concurrently, feed medium #1 was stopped and feed of medium #2 (shown in Example 2) was begun. The feed medium #2 was maintained for the remainder of the fermentation at a fixed rate of 200 ml/hr. The fermentation was ended six hours after the increase of temperature. For further details on the use of single and dual fed batch fermentation see Tsai et al., *J. Indust. Micro.*, 2, 181–187(1987).

The inoculum was prepared by aseptically transferring 200 μl of a frozen 17% glycerol stock culture into 500 ml of Luria broth medium in a 2 liter flask. The culture was grown to a late exponential phase overnight at 30° C. on a rotary shaker. The culture was then transferred into a fermentor containing 8 liters of batch medium. The pH of fermentation was controlled at 7.0 using concentrated ammonium hydroxide and phosphoric acid. Temperature was controlled at 30° C. Dissolved oxygen was kept about 50% air saturation by adjustment of back pressure and agitation rate.

EXAMPLE 1

Recombinant DNA-derived human IL-2 was prepared and purified from a fermentation lot which used yeast extract in the medium. The purified IL-2 is electrophoretically homogeneous and is biologically active (specific activity no less than $10^6$ units/mg).

When the purified protein was analyzed by automated Edman degradation using a gas phase sequenator [Hewick et al., *J. Biol. Chem.*, 256, 7990–7997 (1981) and Lai, *Anal. Chim. Acta*, 163, 243–248 (1984)] for identity and purity, three phenylthiohydantoin (PTH) amino acids were released from the NH$_2$-terminus. These PTH-amino acids were assigned as Ala, Met and Phe["X"]. The yield ratio of Met:Ala:Phe["X"] was 2.9:1.3:1. Further sequence analysis indicated the presence of two recognizable sequences, i.e., Ala-Pro-Thr- and Met-Ala-Pro. The Met and Ala species were expected according to the design of the gene coding for the protein. It is known that the initiator Met, when followed by an amino acid containing small side chain such as alanine, may be processed off after expression [Sherman et al., *Bioessays*, 3, 27–31 (1985)]. The sum of yields for PTH-Met and PTH-Phe["X"] detected in the first cycle of Edman degradation apparently approximated the yield for PTH-Ala in the second cycle, as indicated in Table 1.

In Table 2, the results of automated Edman degradation of recombinant IL-2 synthesized in *E. coli* are presented. About 3.5 nmoles of purified, recombinant human IL-2 synthesized in *E. coli* was applied to an ABi 470A gas phase sequenator, Applied Biosystems, Inc., Foster City, Calif. and samples were analyzed by high performance liquid chromatography (HPLC) (Hunkapiller, et al., Science 219, 650–659 1983). The amino acid designated as X in the text was detected as phenylalanine, and standard PTH-Phe was used in a calculation of yield for this PTH amino acid. Although proline ("Pro") appears in Table 1, phenylthiocarbamyl (PTC) proline was not included in the yield calculation.

TABLE 1

| Cycle No. | PTH-Amino Acid Detected | Yield (pmoles) |
|---|---|---|
| 1 | Ala | 511 |
|   | Met | 921 |
|   | Phe["X"] | 366 |
| 2 | Ala | 1207 |
|   | Pro | 205 |

The results in Table 1 indicate the presence of an unexpected protein species with a sequence of Phe-Ala-Pro at its NH$_2$-terminal, if the observed Phe were the NH$_2$-terminal residue. However, this result is inconsistent with the expected protein sequence as deduced from the designed gene. Thus, it was determined that the phenylalanine-like residue found at the NH$_2$-terminus was an uncommon amino acid (designated as X).

The protein sample was oxidized by treatment with performic acid [Knoper, "Protein Sequence Determination", ed. Needleman 129–130, Springer-Verlag, New York, (1975)]. The HPLC profiles of PTH-amino acids obtained with intact and oxidized proteins were identical. This result suggested that the X amino acid was not a methionine derivative since PTH derivatives of oxidized forms of methionine are well resolved from PTH-Met by the procedure used in this study.

In addition to the observation of X at the NH$_2$-terminus, three unexpected peptide fragments were generated from the tryptic map of the same lot of protein sample (map not shown) and were isolated. These three peptides were identified as $X_1$-$A_2$-$P_3$-$T_4$-$S_5$-$S_6$-$T_8$-$K_9$ (Peptide I), $X_{40}$-$L_{41}$-$T_{42}$-$F_{43}$-$K_{44}$ (Peptide II), and $F_{45}$-$Y_{46}$-$X_{47}$-$P_{48}$-$K_{49}$ (Peptide III) by automated Edman degradation performed as set forth above. Peptides I, II and III differed from three other peptides isolated from the same map at a position where methionine was found. These three methionine peptides were $M_1$-$A_2$-$P_3$-$T_4$-$S_5$-$S_6$-$S_7$-$T_8$-$K_9$ (Peptide IM), $M_{40}$-$L_{41}$-$T_{42}$-$F_{43}$-$K_{44}$ (Peptide IIM), and $F_{45}$-$Y_{46}$-$M_{47}$-$P_{48}$-$K_{49}$ (Peptide IIIM). The results of separation by reverse-phase HPLC of peptides I, II and III and their methionine-containing counterparts, Peptides IM, IIM and IIIM, are given in Table 2 in terms of column retention time (in minutes) and percent recovery.

Isolation and recovery of X amino acid-containing peptides and methionine-containing peptides from a tryptic map of recombinant IL-2 synthesized in *E. coli* was performed by digesting recombinant human IL-2 (0.4 mg/ml) with TPCK-treated trypsin (substrate:enzyme=50:1) in 0.1M NH$_4$HCO$_3$ at pH 7.7 for 4–6 hours. A tryptic map was obtained with a Vydac C$_4$ HPLC column (The Separation Group, Hesperia, Calif.) using 0.1% TFA in H$_2$O as an aqueous mobile phase and 0.1% TFA in 90% acetonitrile as an organic mobile phase. Recovery was calculated using the sum of peak area for the X-peptide and the corresponding methionine-peptide as 100%.

TABLE 2

| Peptide | | Retention time (min.) | Recovery % |
|---|---|---|---|
| I | $X_1$—Ala—Pro—Thr—Ser—Ser—Ser—Thr—$Lys_9$ | 17.2 | 23.9 |
| IM | $Met_1$—Ala—Pro—Thr—Ser—Ser—Ser—Thr—$Lys_9$ | 13.3 | 76.1 |
| II | $X_{40}$—Leu—Thr—Phe—$Lys_{44}$ | 40.3 | 22.7 |
| IIM | $Met_{40}$—Leu—Thr—Phe—$Lys_{44}$ | 38.2 | 77.3 |
| III | $Phe_{45}$—Tyr—X—Pro—$Lys_{49}$ | 39.4 | 26.2 |
| IIIM | $Phe_{45}$—Tyr—Met—Pro—$Lys_{49}$ | 33.8 | 73.8 |

The yield of each X-containing peptide isolated from the map is shown in Table 2 to have been about 30% of that of the corresponding methionine peptide. Thus amino acid X, was detected at more than one place in the IL-2 molecule, and it occurred only at methionine positions.

To identify amino acid X in Peptides I, II and III, and Peptide IIIM, a normal form of peptide III, were subjected to mass spectrometric analysis using fast atom bombardment (FAB) techniques. (Barber et al., Chem. Commu. 325–329 1981). The results are shown in Table 3 wherein the mass ("M") to charge ("Z") ratio ("M/Z") is listed for Peptides I, II, III and IIIM.

Mass spectrometric analysis of X-containing peptides and a methionine peptide isolated from a tryptic map of recombinant IL-2 synthesized in *E. coli* was performed dissolving approximately 4 nmoles of each peptide in 20 ml of 5% acetic acid, after which dissolution, 1.5 nmole aliquots were subjected to mass spectrometric analysis. All mass spectra were recorded on a high field ZAB instrument (VG Analytical Ltd., Manchester, England) fitted with an M-Scan FAB gun (M-Scan Ltd., Ascot, Berkshire, England), operating at 10 KV and 15 microamps, using Xenon gas. Spectra were enhanced using 1 µl of thioglycerol and 0.5 µl of 1M HCl as appropriate.

TABLE 3

| Peptide | Sequence | M/Z | M/Z without X or M | Calculated mass for X or M in Peptide Form |
|---|---|---|---|---|
| I | X—A—P—T—S—S—S—T—K | 891 | 778 | 113 |
| II | X—L—T—F—K | 621 | 508 | 113 |
| III | F—Y—X—P—K | 667 | 554 | 113 |
| IIIM | F—Y—M—P—K | 685 | 554 | 131 |

The results of mass spectrometric analysis as presented in Table 3, suggest that X is leucine, isoleucine, alloisoleucine or norleucine. Amino acid X has the same peptidyl mass of 113 in Peptides I, II, and III. These isomeric forms may be unambiguously distinguished from methionine and its derivatives by mass spectrometry.

To further identify the X amino acid, the PTH form of amino acid X was obtained from automated Edman degradation of intact IL-2 followed by HPLC separation on columns. The resulting HPLC profiles were compared to those of authentic PTH-norleucine, PTH-leucine, PTH-isoleucine and PTH-alloisoleucine. PTH-amino acid separation by HPLC using a C18 column was performed generally according to the method described in User Bulletin No. 12, Applied Biosystems, Foster City, Calif. (Aug. 15, 1985). The HPLC profiles of PTH-X amino acid were identical to those of PTH-norleucine in both analytical sytems (chromatograms not shown). Amino acid X was thus determined to be norleucine, and about 30% of methionine residue at positions 1, 40 and 47 of the recombinant IL-2 protein was therefore shown to be replaced by norleucine.

There are several possible sources of norleucine incorporated into the preparation of recombinant IL-2. One possible source was foreign norleucine provided in the culture medium. However, when a feed stock extract and a complete HCl hydrolysate of the feed stock were analyzed for norleucine by amino acid analysis, norleucine was not detected. Another possible source was that norleucine was biosynthetically produced by the host strain of *E. coli*.

The discovery of norleucine at the $NH_2$terminus described here is of particular interest. It suggests that norleucine may replace methionine as the initiator in the process of protein synthesis.

It is reasonable to assume that norleucine may also be used as a substrate for methionyl tRNA deformylase due to the molecular similarity between norleucine and methionine.

EXAMPLE 2

In a study of the relationship of fermentation conditions to norleucine incorporation into IL-2, the recombinant plasmid containing *E. coli* cells were grown in a fermentor containing a batch medium as described below.

Medium composition in single feed fed batch fermentation

| Chemicals | Batch Medium | Feed Medium |
|---|---|---|
| glucose | 5 g/L | 430 g/L |
| bactotryptone | 25 g/L | 110 g/L |
| yeast extract | 5 g/L | — |
| $K_2HPO_4$ | 7 g/L | — |
| $KH_2PO_4$ | 8 g/L | — |
| $(NH_4)_2SO_4$ | 4 g/L | 5 g/L |
| $MgSO_4.7H_2O$ | 1 g/L | 8 g/L |
| *trace metals solution | 2 ml/L | 10 ml/L |
| **vitamin solution | 2 ml/L | 10 ml/L |

Medium composition in dual feed fed batch fermentation.

| Chemical | Batch Medium | Feed Medium #1 | Feed Medium #2 |
|---|---|---|---|
| Glucose | 5 g/L | 430 g/L | 300 g/L |
| yeast extract | 5 g/L | 50/L | 110 g/L |
| bactotryptone | — | — | 220 g/L |
| $K_2HPO_4$ | 7 g/L | — | — |
| $KH_2PO_4$ | 8 g/L | — | — |
| $(NH_4)_2SO_4$ | 4 g/L | 110 g/L | — |
| $MgSO_4.7H_2O$ | 1 g/L | 8 g/L | — |
| *Trace metal solution | 2 ml/L | 10 ml/L | — |
| *Vitamin solution | 2 ml/L | 10 ml/L | — |

*Trace metals solution: $FeCl_3.6H_2O$, 27 g/L; $ZnCl_2.4H_2O$, 2 g/L; $CaCl_2.6H_2O$, 2 g/L; $Na_2MoO_4.2H_2O$, 2 g/L; $CuSO_4.5H_2O$, 1.9 g/L; $H_3BO_3$, 0.5 g/L; concentrated HCl, 100 ml/L.
**Stock vitamin solution: riboflavin, 0.42 g/L; pantothenic acid, 5.4 g/L; niacin, 6 g/L; pyridoxine, 1.4 g/L; biotin, 0.06 g/L; and folic acid, 0.04 g/L.

extract (YE) was added to the batch medium. Cells were harvested and examined for norleucine incorporation as above and cell density, yield and percent of norleucine incorporation were considered. The results are provided in Table 5.

In minimal medium fermentation norleucine incorporation may be as high as 19% as shown in Table 5. By comparison, in rich organic nitrogen medium fermentation, norleucine incorporation decreased to an average level of 3% as indicated in Table 4.

TABLE 4

The Level of Norleucine Incorporation in Purified IL-2 Protein Under Various Rich Medium Fermentation Conditions

| Experiments | Fermentation Run No. | Feed Cond. | Cell Density (OD) | Yield of IL-2 mg/L/OD | % of Norleucine |
|---|---|---|---|---|---|
| High Disolved Oxygen | 796-13 | (D) | 69 | 75–80 | 1.4 |
| Low Disolved Oxygen | 825-9 | (D) | 48 | 50–55 | 1.4 |
| High Product Yield | 823-9 | (D) | 64 | 85–90 | 2.3 |
| Low Product Yield | 896-6 | (D) | 60 | 45–50 | 1.5 |
| Optimal Glucose | 825-8 | (D) | 58 | 50–55 | 3.0 |
| Low Glucose | 854-6 | (D) | 60 | 35–40 | 4.2 |
| High Cell Density | 796-12 | (S) | 75 | 65–70 | 1.6 |
| | 825-7 | (S) | 75 | 40–45 | 2.3 |
| | 897-5 | (D) | 79 | 50–55 | 1.0 |
| Low Cell Density | 896-11 | (D) | 41 | 40–50 | 4.3 |
| | 896-5 | (D) | 45 | 65–70 | 1.0 |
| | 823-7 | (S) | 47 | 40–45 | 4.7 |
| High Acetate Level | 896-11 | (D) | 41 | 45–50 | 4.3 |
| | 896-6 | (D) | 60 | 45–50 | 1.5 |
| | 896-5 | (D) | 45 | 65–70 | 1 |
| Low Acetate Level | 897-6 | (S) | 72 | 50 | 1 |
| | 825-8 | (D) | 56 | 45–50 | 3 |

The degree of incorporation of norleucine into IL-2 under fermentation in minimal medium was examined. The recombinant plasmid containing *E. coli* cells described above were inoculated into a fermentor containing a minimal batch medium, and supplied with a feed medium at a rate and temperature previously outlined. In some runs 0.5% yeast

TABLE 5

The Level of Norleucine Incorporation Into Purified IL-2 Under Minimal Medium Fermentation

| Experiments | Fermentation Run No. | Fermentation Cond. | Cell Density (OD) | Yield of IL-2 mg/L/OD | % of Norleucine |
|---|---|---|---|---|---|
| Minimal Medium | 867-11 | Minimal medium (0.5% YE in batch) | 52 | 60 | 12 |
| Minimal Medium | 884-5 | Minimal medium (0.5% YE in batch) | 49 | 40 | 15 |
| Minimal Medium | 883-12 | Minimal medium | 37 | 35 | 19 |

Norleucine is also found in other recombinant proteins (such as IFN-γ, GCSF and IFN-αCon) when minimal medium is used for their fermentative production as shown in Table 6. The degree of incorporation of norleucine into α-consensus interferon, γ-interferon and hGCSF under fermentation in minimal medium was also examined. Recombinant plasmid containing E. coli cells were inoculated into a fermentor containing a minimal batch medium and supplied with a feed medium at a rate and temperature as previously described. In some runs 0.5% yeast extract (YE) was added to the batch medium. Cells were harvested and examined for norleucine incorporation as above and cell density, yield and percent of norleucine incorporation were considered. The results are provided in Table 6.

As reflected in Table 4, the occurrence in recombinant gene expression products of norleucine incorporation, particularly at high levels, was found to be mainly dependent on the nitrogenous nutrient condition of fermentation.

located on the chromosome. The ability of the cI gene to control the $P_L$ promoter is not complete. This results in a measurable basal expression level for the recombinant gene. The hGCSF protein is synthesized at a slow rate (2.5 mg/L/OD/hr) at 30° C. When the culture is shifted to 42° C., the cI gene is thermally denatured. As the $P_L$ promoter became fully functioning, the rate of GCSF synthesis also increased to 7 mg/L/OD/hr. An increase in norleucine incorporation was found to correspond to an increase in hGCSF synthesis. Norleucine incorporation was less than 1% at the slow rate of hGCSF synthesis and 6% at the higher rate of protein synthesis.

TABLE 6

Levels of Norleucine Incorporation Into Recombinant Proteins of α Consensus Interferon; γ Interferon and GCSF Under Minimal Medium Fermentation

| Experiments | Fermentation Run No. | Fermentation Cond. | Cell Density (OD) | Yield of Recombinant Protein IL-2 mg/L/OD | % of Norleucine |
|---|---|---|---|---|---|
| α Consensus Interferon | 905-13 | Minimal medium (0.5% YE in batch) | 81 | 50 | trace |
| γ-Interferon | 907-9 | Minimal medium (0.5% YE in batch) | 84 | 70 | 6 |
| GCSF | 005-5 | Minimal medium (0.05% YE in batch) | 55 | 40 | 18 |
| GCSF | 973-6 | Minimal medium (0.5% YE in batch) | 40 | 65–40 | 10 |

EXAMPLE 3

To evaluate whether the host cell was a contributing factor to norleucine incorporation, host cells without plasmids were evaluated using the same conditions as host cells containing a recombinant plasmid. In fermentation run designated Run No. 885-11 incorporation of norleucine in the major protein of host cells was investigated. E. coli cells of the strain used for polypeptide expression, not containing any recombinant plasmid, were exposed to fermentation and medium conditions as previously described. The cells reached an optical density of 65 before the cells were harvested and processed for evaluation of norleucine incorporation.

No norleucine was detected in E. coli major protein from the cells.

EXAMPLE 4

High intensity recombinant protein translation of the sort present during the thermoinduction was examined as a potential cause for norleucine incorporation. During a period of high intensity recombinant-protein translation, it is very possible that the amino acid pool decreases. The decrease of the leucine amino acid pool may activate the leucine biosynthetic pathway which in turn may lead to norleucine biosynthesis. Concurrently, a lowering of the methionine pool may allow norleucine to be used in translation.

Evidence that the level of norleucine incorporation is related to the rate of recombinant protein synthesis has been obtained using an E. coli strain (FM-6) containing the hGCSF gene on a walkaway plasmid (plasmid 1156). The cI gene which controls the $P_L$ promoter on this plasmid is

EXAMPLE 5

Enzymes in the leucine biosynthetic pathway are illustrated in FIG. 1. These enzymes are isopropylmalate synthetase, isopropylmalate dehydratase, isopropyl malate dehydrogenase and transaminase. The enzymes have a broad range of substrate specificity. The initial substrate may be α-ketobutyrate or α-ketovalarate. Through enzymatic reaction, the straight chain of the α-keto acid is elongated by addition of one carbon in each cycle at the expense of an acetyl CoA. Norleucine is derived directly from α-ketocaproic acid (a six carbon straight chain a-keto acid) through a transamination reaction.

The degree of incorporation of norvaline and norleucine into IL-2 under fermentation in minimal and rich medium respectively, was also examined. For norvaline, 0.37 g/L of norvaline was added to the fermentor batch, 1.25 g/L was added in the feed medium. For norleucine, 0.25 g/L of norleucine was added to the fermentor batch, 1.25 g/L was added in the feed medium. The recombinant plasmid-containing E. coli cells were inoculated into a fermentor containing a minimal or rich batch medium and supplied with a feed medium at a rate and temperature as previously described. In some runs 0.5% yeast extract (YE) was added to the batch medium. Cells were harvested and examined for norleucine incorporation as above and cell density, yield and percent of norleucine incorporation were considered. The results are provided in Table 7.

The level of norleucine incorporation into IL-2 reached 45% when norvaline was supplemented to the fermentation medium. The norvaline served as a source of α-ketovalerate to bacterial cells after deamination. The α-ketovalarate forms norleucine through the above pathway and is then heavily incorporated into IL-2 protein.

TABLE 7

The Effect of Nor-Valine & Norleucine Added
to the Fermentation Medium on the Level
of Norleucine Incorporation Into IL-2 Protein

| Experiments | Fermentation Run No. | Fermentation Cond. | Cell Density (OD) | Yield of IL-2 mg/L/OD | % of Norleucine |
|---|---|---|---|---|---|
| Addition Of Novaline | 885-6 | Minimal (0.5% YE in batch) | 42 | 35 | 40 |
| Addition Of Norleucine | 841-13 | Rich medium | 45–50 | 60 | 40 |

EXAMPLE 6

The degree of incorporation of norleucine into IL-2 and G-CSF under fermentation in minimal or rich medium containing norleucine and/or methionine was also examined. The recombinant plasmid containing *E. coli* cells were inoculated into a fermentor containing a minimal or rich batch medium and supplied with a feed medium at a rate as previously described. For the series of fermentation runs listed in Table 8, the batch medium was 8 L, the feed medium ranged from 1 L to 4.5 L. In run 863-11, 3 g of leucine were present in the batch medium, 20 g/3 L were added to the feed medium. In runs 884-11 and 829-6, 5 g of leucine were present in the batch medium, 20 g/4 L were added to the feed medium. In run 967-13, 15 g/L of leucine were added to the second feed medium. In run 884-6, 5 g/8 L of methionine were present in the batch medium, 20 g/4.5 L were added to the feed medium. In run 893-6, 3 g/8 L of norleucine and 5 g/8 L of methionine were present in the batch medium; 5 g/4 L of norleucine and 25 g/4 L of methionine were added to the feed medium. In run 893-5, 3 g/8 L of leucine and 5 g/8 L of methionine were present in the batch medium, 10 g/4 L of leucine and 20 g/4 L of methionine were added to the feed medium. In run 958-10, using a dual feed system, 2 g/8 L of leucine and 2 g/8 L methionine were present in the batch medium, 4 g/L of leucine and 5 g/L of methionine were added to a first feed medium; 10 g/L of leucine and 30 g/L of methionine were added in an additional feed. In some runs 0.5% yeast extract ("YE") was added to the batch medium. Cells were harvested and examined for norleucine incorporation as above and cell density, yield and percent of norleucine incorporation were considered. The results are provided in Table 8.

As shown in Table 8, the addition of leucine to minimal medium fermentation decreased the incorporation of norleucine to a level of 2%. This may be mainly due to leucine feedback inhibition of the enzyme isopropylmalate synthetase which effectively suppresses the biosynthesis of norleucine. The results in Table 8 substantiate the fact that synthesis of norleucine is occurring through the pathway proposed in FIG. 1.

The addition of methionine to minimal medium fermentation also lowered the incorporation of norleucine. Because methionine presumably serves as a better substrate for methionyl tRNA synthetase, methionine may effectively compete with norleucine to drive down the level of incorporation of norleucine.

An effective way to control norleucine incorporation was to supplement the bacterial culture with both methionine and leucine during the thermoinduction period. In this way incorporation of norleucine may be reduced to an undetectable level.

TABLE 8

Fermentation Control of Norleucine
Incorporation by Adding Leucine, Methionine
or Both Amino Acids in Minimal Medium Fermentation

| Experiments | Fermentation Run No. | Fermentation Cond. | Cell Density (OD) | Yield of IL-2 mg/L/OD | % of Norleucine |
|---|---|---|---|---|---|
| The Addition of Leucine | 863-11 | Rich medium | 61 | 40 (IL-2) | 0.93 |
| The Addition of Leucine | 884-11 | Minimal medium (0.5% YE in batch) | 30 | 30 (IL-2) | 1.2 |
| The Addition of Leucine | 829-6 | Minimal medium (0.5% YE in batch) | 56 | 45–50 (IL-2) | 2.6 |
| The Addition of Leucine | 967-13 | Minimal medium | 48 | 45–50 (GCSF) | 2 |
| The Addition of Methionine | 884-6 | Minimal medium (0.5% YE in batch) | 45 | 60–65 (IL-2) | 2.5 |
| The Addition of Methionine & Norleucine | 893-6 | Minimal medium (0.5% YE in batch) | 52 | 40–45 (IL-2) | 1.4 |
| The Addition of Leucine & Methionine | 893-5 | Minimal medium (0.5% YE in batch) | 55 | 45–50 (IL-2) | 0 (undetectable) |
| The Addition of Leucine & Methionine | 958-10 | Minimal medium (0.5% YE in batch) | 46 | 45–50 (GCSF) | 0 (undetectable) |

EXAMPLE 7

A genetic approach to the prevention of norleucine accumulation in recombinant proteins may be based on blocking the pathway that gives rise to norleucine, i.e., the leucine biosynthetic pathway. A mutation inactivating the leuA gene was chosen because the functional state of the enzyme can be readily confirmed biochemically by assaying crude cell extracts with a convenient colorimetric method.

A leuA mutant, *E. coli* CV512 harboring leu A371, was obtained from the *E. coli* Genetic Stock Center, Yale University, New Haven, Conn.

The Hfr strain P801 leu$^+$, Tc$^S$ (tetracycline sensitive) was transduced to tetracycline resistance using phage P1 grown on KJ839 thr::Tn10mh. Transductants were scored for the retention of the ara-41 gene. The desired transductant was called KJ969 and possessed the genotype Hfr P801 thr::Tn10mh, ara-41.

KJ 969 was mated with Amgen #393Sm$^R$ (streptomycin resistant). Exconjugants were selected on Luria agar containing tetracycline and streptomycin and then scored for the Ara phenotype. This strain was transduced to Ara$^+$ using P1 harvested on CV512 ara, leuA371, Ara$^+$ transductants were scored for the Leu phenotype. Some were Thr$^+$ Tc$^S$ indicating that the transduction event had replaced the entire chromosomal segment from thr to leu, a distance (1.3 minutes) approaching the limit of cotransduction capable by P1. The strain, Amgen #393Sm$^R$, leuA 371 was called KJ966 and was deposited with the American Type Culture Collection (A.T.C.C.) on Mar. 1, 1991 under accession no. 68541.

KJ966 was transformed with plasmids pMW1 and pCFM536-IL2ala to create a walkaway production strain for interleukin 2-ala analogue (Amgen strain #656). The leu$^+$ revertant was required as a control strain and was created by P1 transduction (Amgen strain #679). The GCSF leuA production strain was prepared similarly except that FM6 was used as the host. FM6 carries on its chromosome the cI857 thermosensitive phage lambda repressor gene. The strain was transformed with the plasmid pCFM536-GCSF and was assigned Amgen strain #625. The leu$^+$ revertant was created by transduction and assigned Amgen strain #627.

Both strains #625 and #627 were grown in 10 liter fermentations. For the leu+ revertant, #627, the yield of GCSF was 30 mg/ODL and the norleucine content in the GCSF was 2.1%. For the leuA mutant, #625, the yield of GCSF was 25 mg/ODL and the norleucine content was undetectable.

Under minimal medium fermentation, the leuA mutant produced GCSF protein with no detectable norleucine. By comparison, the leuA+ revertant generates 2.9% of norleucine incorporated under identical fermentation conditions.

Although the present invention has been described in terms of a preferred embodiment, it is understood that variations and improvements will occur to those skilled in the art upon consideration of the present invention.

Accordingly, it is intended that all such variations and improvements come within the scope of the present invention as claimed.

What is claimed is:

1. A method of inhibiting incorporation of norleucine into an expression product of recombinant DNA within a host cell, the method comprising the steps of:
    a) culturing host cells in a culture medium to express a product of recombinanat DNA wherein the expression product has detectable norleucine;
    b) modifying the culture medium in (a) such that norleucine incorporation into the expression product is inhibited; and
    c) culturing cells in the modified medium to express a product of recombinant DNA wherein the expression product is free of detectable norleucine.

2. The method of claim 1 wherein the host cell synthesizes norleucine by a pathway characteristic of the norleucine biosynthetic pathway of procaryotes.

3. The method of claim 1 wherein step (b) comprises modifying the culture medium by adjusting a concentration of an amino acid selected from the group consisting of leucine and methionine and mixtures thereof, which concentration after adjusting equal to or greater than the concentration effective in preventing norleucine incorporation into the expression product of recombinant DNA by the host cell.

4. The method of claim 3 wherein the effective concentration of the amino acid is less than 2 g/L and the host cell is *Escherichia coli*.

5. The method of claim 4 wherein the adjusted concentration of the amino acid in the medium is equal to or greater than 2 g/L and the host cell is *Escherichia coli*.

6. The method of claim 3 wherein the amino acid is leucine.

7. The method of claim 3 wherein the amino acid is methionine.

8. The method of claim 3 wherein the expression product is selected from the group consisting of interleukin-2,

TABLE 9

The norleucine Incorporation
In LeuA Mutant and its Revertant
Under Minimal Medium Fermentation

| Experiments | Fermentation Run No. | Fermentation Cond. | Cell Density (OD) | Yield of GCSF mg/L/OD | % of Norleucine |
|---|---|---|---|---|---|
| LeuA Mutant | 971-3 | Minimal medium (0.5% YE in batch) | 38 | 20–25 | 0 |
| LeuA Revertant | 971-5 | Minimal medium (0.5% YE in batch) | 46 | 30 | 2.1 |

A mutation at the leuA gene to inactivate the enzyme isopropylmatate synthetase can block the norleucine biosynthetic pathway. This led to a complete elimination of norleucine biosynthesis and incorporation.

gamma-interferon, consensus interferon and granulocyte colony stimulating factor.

9. A method for inhibiting incorporation of norleucine into an expression product of recombinant DNA within a host cell, the method comprising the steps of:

a) culturing host cells to express a product of recombinant DNA wherein the expression product has detectable norleucine;

b) modifying the host cell in (a) such that one or more genes of a leucine biosynthetic pathway are inactivated; and c) culturing the modified host cells to express a product of recombinant DNA wherein the expression product is free of detectable norleucine.

10. The method of claim 9 wherein the host cell has a mutation which inactivates the gene encoding isopropylmalate synthetase.

11. The method of claim 10 wherein the host cell is *Escherichia coli* stain #625.

12. A method for promoting incorporation of norleucine into an expression product of recombinant DNA within a host cell, the method comprising the steps of:

a) culturing host cells in a culture medium to express a product of recombinant DNA;

b) modifying the culture medium in (a) such that norleucine incorporation into the expression product is increased; and c) culturing host cells in the modified medium to express a product of recombinant DNA wherein the product has increased levels of norleucine compared to the product in (a).

13. The method of claim 12 wherein the host cell synthesizes norleucine by a pathway characteristic of the norleucine biosynthetic pathway of procaryotes.

14. The method of claim 12 wherein step (b) comprised modifying the culture medium by adjusting a concentration of an amino acid selected from the group consisting of leucine and methionone and mixtures thereof, which concentration after adjusting is less than the concentration effective in preventing norleucine incorporation into the expression product of recombinant DNA by the host cell.

15. The method of claim 14 wherein the effective concentration of the amino acid is less than 2 g/L and said host cell is *Escherichia coli*.

16. The method of claim 14 wherein the adjusted concentration of the amino acid introduced into the medium is less than 2 g/L and the host cell *Escherichia coli*.

17. The method of claim 14 wherein the amino acid is leucine.

18. The method of claim 14 wherein the amino acid is methionine.

19. The method of claim 12 wherein the expression product is selected from the group consisting of interleukin-2, gamma-interferon, consensus interferon and granulocyte colony stimulating factor.

* * * * *